(12) United States Patent
Kim et al.

(10) Patent No.: US 9,811,063 B2
(45) Date of Patent: Nov. 7, 2017

(54) APPARATUS AND METHOD OF DISCRIMINATING REFORMULATED FUEL

(71) Applicant: Electronics and Telecommunications Research Institute, Daejeon (KR)

(72) Inventors: Wan Joong Kim, Daejeon (KR); Mun Youn Jung, Daejeon (KR)

(73) Assignee: ELECTRONICS AND TELECOMMUNICATIONS RESEARCH INSTITUTE, Daejeon (KR)

(*) Notice: Subject to any disclaimer, the term of this patent is extended or adjusted under 35 U.S.C. 154(b) by 274 days.

(21) Appl. No.: 14/618,642

(22) Filed: Feb. 10, 2015

(65) Prior Publication Data

US 2015/0346133 A1    Dec. 3, 2015

(30) Foreign Application Priority Data

May 27, 2014 (KR) ........................ 10-2014-0063433

(51) Int. Cl.
| | |
|---|---|
| G01N 27/22 | (2006.01) |
| G05B 15/02 | (2006.01) |
| G01N 33/28 | (2006.01) |
| B60K 15/03 | (2006.01) |

(52) U.S. Cl.
CPC ............ *G05B 15/02* (2013.01); *G01N 27/22* (2013.01); *G01N 33/2829* (2013.01); *B60K 2015/0319* (2013.01); *B60K 2015/0321* (2013.01); *B60K 2015/03361* (2013.01)

(58) Field of Classification Search
CPC .... G05B 15/02; G01N 33/2829; G01N 27/22; B60K 2015/0319; B60K 2015/0321; B60K 2015/03361

USPC ................................................. 141/83, 94, 98
See application file for complete search history.

(56) References Cited

U.S. PATENT DOCUMENTS

| | | | | | |
|---|---|---|---|---|---|
| 2,725,501 | A | * | 11/1955 | Sihvonen | G01L 23/22 313/313 |
| 5,231,358 | A | * | 7/1993 | Kapsokavathis | G01N 33/2852 324/663 |
| 5,353,641 | A | * | 10/1994 | Tang | G01P 15/125 73/514.18 |
| 6,121,628 | A | * | 9/2000 | Rising | F23N 5/082 250/573 |
| 6,125,696 | A | * | 10/2000 | Hannan | G01F 23/265 324/658 |
| 7,030,629 | B1 | * | 4/2006 | Stahlmann | G01N 33/26 324/663 |

(Continued)

FOREIGN PATENT DOCUMENTS

| | | | | | |
|---|---|---|---|---|---|
| JP | 05010196 | A | * | 1/1993 | ............ F02D 45/00 |
| KR | 10-1130907 | B1 | | 3/2012 | |
| KR | 20140068398 | A | * | 6/2014 | ............ B60K 15/06 |

*Primary Examiner* — Nicolas A Arnett

(57) ABSTRACT

Provided is an apparatus of discriminating reformulated fuel, which includes a fuel sensing unit including first and second electrode plates which are spaced and face each other, and a measuring part connected to the first and second electrode plates; a fuel control valve unit including a control valve part blocking the fuel passage and a second actuator driving the control valve part; and a control unit connected to the measuring part and the second actuator, and operating the second actuator based on a capacitance measured from the measuring part.

12 Claims, 5 Drawing Sheets

(56) References Cited

U.S. PATENT DOCUMENTS

| | | | |
|---|---|---|---|
| 7,466,147 B2 * | 12/2008 | Stahlmann | G01N 27/226 324/663 |
| 7,634,945 B2 * | 12/2009 | Champion | G01F 23/268 73/291 |
| 7,800,379 B2 * | 9/2010 | Hernandez | G01N 27/226 324/663 |
| 7,981,554 B2 * | 7/2011 | Sato | H01M 8/04089 429/408 |
| 9,335,314 B2 * | 5/2016 | Ryu | G01N 21/3577 |
| 2006/0088756 A1 * | 4/2006 | Sato | H01M 8/04089 429/410 |
| 2012/0174894 A1 * | 7/2012 | Hagen | F02M 25/08 123/447 |
| 2013/0029355 A1 | 1/2013 | Cho et al. | |
| 2013/0257457 A1 * | 10/2013 | Kato | G01N 27/22 324/663 |
| 2015/0136959 A1 * | 5/2015 | Ryu | G01N 21/3577 250/227.11 |
| 2016/0123860 A1 * | 5/2016 | McBrien | G01F 1/00 702/25 |
| 2016/0258895 A1 * | 9/2016 | Kato | F02M 37/103 |

\* cited by examiner

APPARATUS AND METHOD OF DISCRIMINATING REFORMULATED FUEL

CROSS-REFERENCE TO RELATED APPLICATIONS

This U.S. non-provisional patent application claims priority under 35 U.S.C. §119 of Korean Patent Application No. 10-2014-0063433, filed on May 27, 2014, the entire contents of which are hereby incorporated by reference.

BACKGROUND OF THE INVENTION

The present invention disclosed herein relates to an apparatus and method of discriminating reformulated fuel.

As shops selling reformulated fuels have recently been increased, numbers of shops and cases prosecuted also become increasing. Reformulated gasoline is produced by mixing gasoline with toluene, methanol, etc., and reformulated diesel is produced by mixing diesel with kerosene which is lower in price than diesel. Also, lubricating oil or the like is added to adjust viscosity. Reformulated gasoline and reformulated diesel badly affect on car engines and the environment. Especially, in case of reformulated diesel, the boiling points of diesel and kerosene are different, which may cause damage to engines and vehicle fire and explosion. Furthermore, reformulated fuel generates a large quantity of carcinogens during combustion thereof, which results in environmental pollution and health threat.

SUMMARY OF THE INVENTION

The present invention provides an apparatus of discriminating and blocking reformulated fuel.

The present invention also provides a method of discriminating reformulated fuel.

The object of the present invention is not limited to the aforesaid, but other objects not described herein will be clearly understood by those skilled in the art from descriptions below.

Embodiments of the present invention provide an apparatus of discriminating reformulated fuel including a fuel sensing unit including first and second electrode plates which are spaced and face each other, and a measuring part connected to the first and second electrode plates; a fuel control valve unit including a control valve part blocking the fuel passage and a second actuator driving the control valve part; and a control unit connected to the measuring part and the second actuator, and operating the second actuator based on a capacitance measured from the measuring part.

In some embodiments, the fuel sensing unit may be disposed closer to a fuel inlet of the fuel passage than the fuel control valve unit.

In other embodiments, the first electrode plate and the second electrode plate may be disposed in parallel with a surface of the fuel passage.

In still other embodiments, the fuel sensing unit may further include a first actuator allowing the second electrode plate to move toward the first electrode plate to reduce a separation distance between the first electrode plate and the second electrode plate.

In even other embodiments, the first and the second electrode plates may be made of aluminum.

In yet other embodiments, the fuel control valve unit may further include a first connecting part and a second connecting part which face each other and respectively disposed on one side wall and the other side wall of the fuel passage, wherein the first connecting part and the second connecting part have a space therebetween, and the driven control valve part is disposed in the space between the first and second connecting parts to block the fuel passage.

In further embodiments, the apparatus may further include a dashboard which is connected to the control unit and has a warning lamp receiving a signal from the control unit to indicate a warning when reformulated fuel is injected.

In other embodiments of the present invention, a method of discriminating reformulated fuel including: adjusting a separation distance between a first electrode plate and a second electrode plate by allowing a control unit to operate a first actuator of a fuel sensing part, when fuel is injected to a fuel passage; measuring a capacitance of the fuel by a measuring part when the fuel is disposed between the first electrode plate and the second electrode plate; delivering the capacitance value measured from the measuring part to the control unit; and blocking the fuel passage by the control valve part by allowing the control unit to operate a second actuator of the fuel control valve unit based on the capacitance value.

In some embodiments, the method may further include generating a warning signal by the control unit, and delivering the warning signal to a user through a warning lamp of a dashboard based on the capacitance vale.

In other embodiments, the method may include setting a capacitance value of genuine fuel in the control unit, and operating the second actuator by determining a capacitance value of reformulated fuel which differs from that of the genuine fuel by the control unit.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Figure 1:
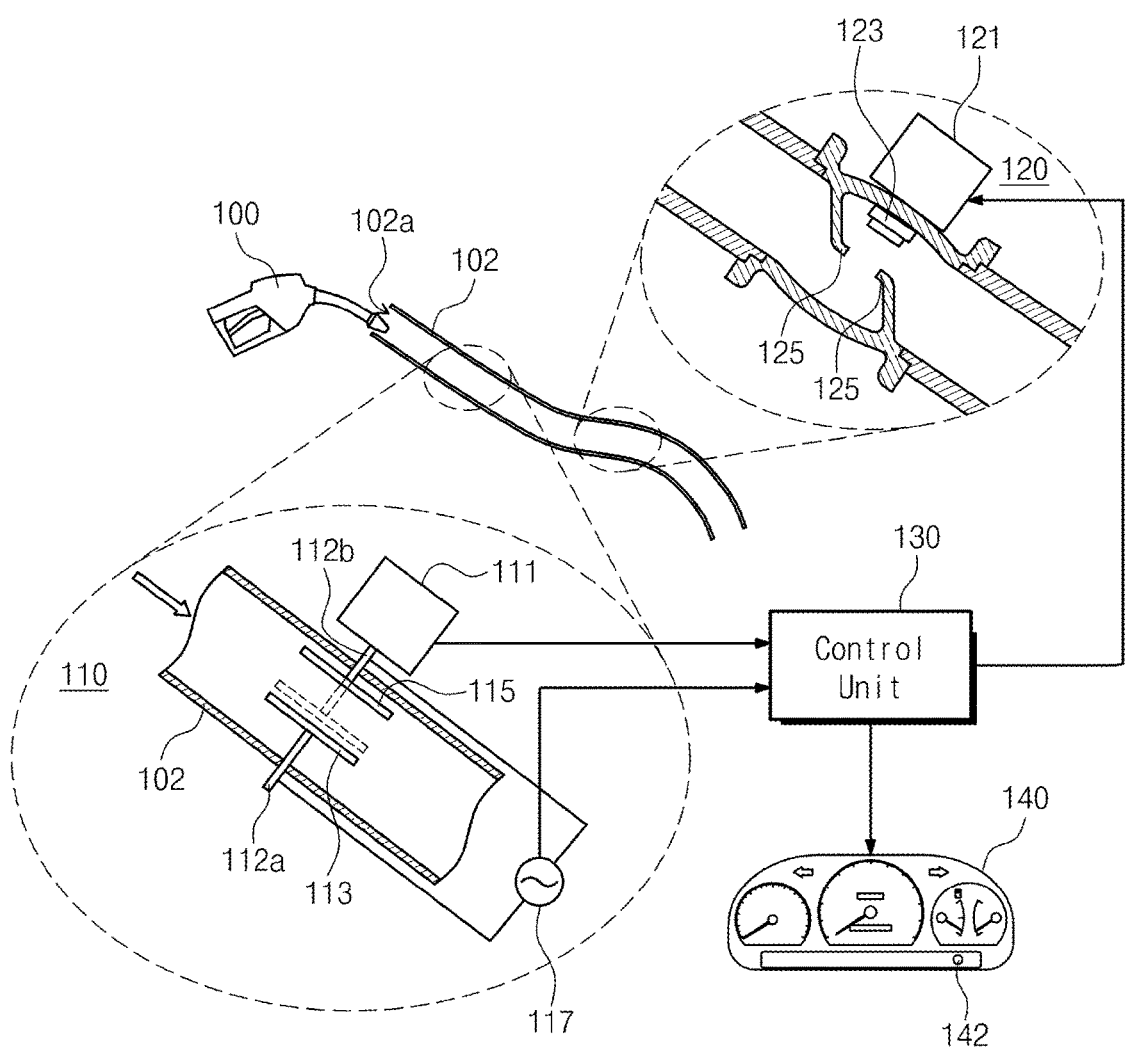
FIG. 1 is a view illustrating an apparatus of discriminating reformulated fuel according to an embodiment of the present invention.

Preferred embodiments of the present invention will be described below in more detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Further, the present invention is only defined by scopes of claims. Like reference numerals refer to like elements throughout.

In the following description, the technical terms are used only for explaining a specific exemplary embodiment while not limiting the present disclosure. The terms of a singular form may include plural forms unless referred to the contrary. The meaning of "include," "comprise," "including," or "comprising," specifies a property, a region, a fixed number, a step, a process, an element and/or a component but does not exclude other properties, regions, fixed numbers, steps, processes, elements and/or components.

The embodiment in the detailed description will be described with sectional views and/or plain views as ideal exemplary views of the present invention. Also, in the figures, the dimensions of layers and regions are exaggerated for clarity of illustration. Accordingly, shapes of the exemplary views may be modified according to manufacturing techniques and/or allowable errors. Therefore, the embodiments of the present invention are not limited to the specific shape illustrated in the exemplary views, but may include other shapes that may be created according to manufacturing processes. For example, an etched region having a right angle illustrated in the drawings may have a round shape or a shape having a predetermined curvature. Areas exemplified in the drawings have general properties, and are used to illustrate a specific shape of a semiconductor package region. Thus, this should not be construed as limited to the scope of the present invention.

Figure 2:
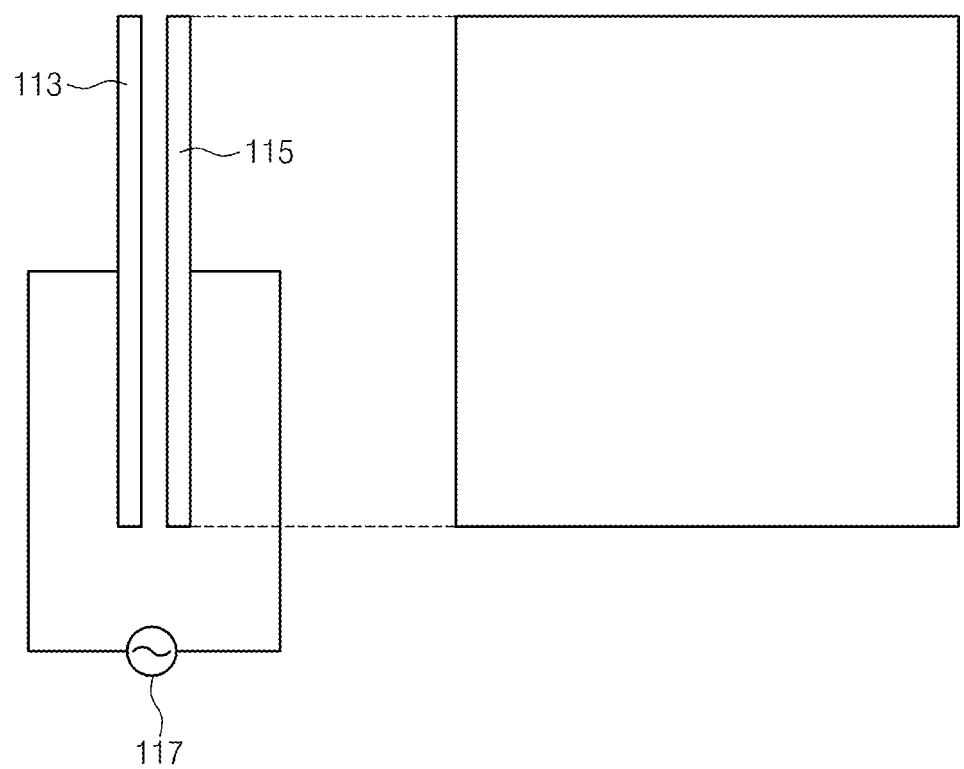
FIG. 2 is an enlarged view illustrating electrodes of an apparatus of discriminating reformulated fuel according to an embodiment of the present invention.
Figure 3:
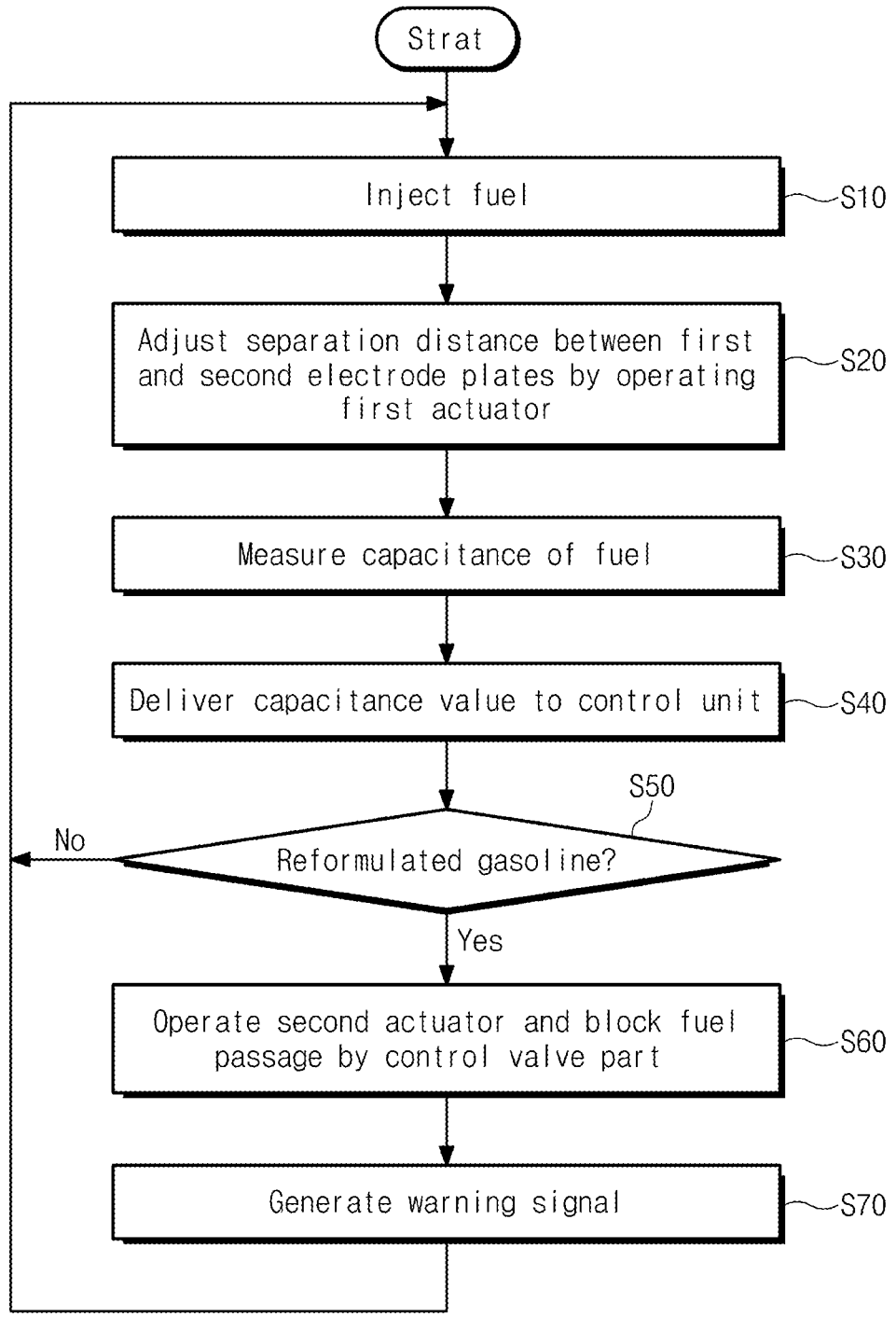
FIG. 3 is a flowchart illustrating a method of discriminating reformulated fuel according to an embodiment of the present invention.

FIG. 1 is a view illustrating an apparatus of discriminating reformulated fuel according to an embodiment of the present invention. FIG. 2 is an enlarged view illustrating an electrode of an apparatus of discriminating reformulated fuel according to an embodiment of the present invention. FIG. 3 is a flowchart illustrating a method of discriminating reformulated fuel according to an embodiment of the present invention.

Referring to FIG. 1, fuel may be injected into a fuel passage 102 through a fuel inlet 102a using a fuel dispensing nozzle 100. A fuel sensing unit 110 and a fuel control valve unit 120 may be disposed in the fuel passage 102. The fuel sensing unit 110 may be disposed closer to the fuel inlet 102a than the fuel control valve unit 120.

The fuel sensing unit 110 may include a first actuator 111, a first electrode plate 113, and a second electrode plate 115. The first electrode plate 113 may be fixed to a first supporting pillar 112a, and the second electrode plate 115 may be fixed to a second supporting pillar 112b. The first actuator 111 may be disposed outside the fuel passage 102.

Referring to FIGS. 1 and 2 together, the first and the second electrode plates 113 and 115 may be spaced apart from each other by a predetermined distance and disposed in parallel with the surface of the fuel passage 102. The first electrode plate 113 and the second electrode plate 115 may have a separation distance of about 10 mm therebetween. The first actuator 111 is connected to a control unit 130, and also connected to the second electrode plate 115. The second electrode plate 115 may be moved by the first actuator 111. For instance, the second electrode plate 115 may move toward the first electrode plate 113 to reduce the separation distance between the first electrode plate 113 and the second electrode plate 115. For instance, the second electrode plate 115 may move toward the first electrode plate 113 to have the separation distance of about 0.1 mm between the first electrode plate 113 and the second electrode plate 115. The first and the second electrode plates 113 and 115 may have the area of about 80 mm×about 80 mm. The separation distance between the first and the second electrode plates 113 and 115 and the areas of the first and the second electrode plates 113 and 115 are not limited to the above, and may vary with measuring conditions. The first and the second electrode plate 113 and 115 may be made of aluminum. The first and the second electrode plates 113 and 115 are connected through alternating current voltage, so that the capacitance of the fuel flowing between the first and the second electrode plates 113 and 115 may be measured by a measuring part 117. For instance, an alternating current of about 100 kHz may be applied to the first and the second electrode plates 113 and 115.

The fuel control valve unit 120 may include a control valve part 123 coupled to the second actuator 121, and connecting parts 125. The second actuator 121 may be disposed outside the fuel passage 102 and the control valve part 123 may be disposed in the fuel passage 102. One of the connecting parts 125 may be disposed on one sidewall of the fuel passage 102, and the other of the connecting parts 125 may be disposed on the other sidewall of the fuel passage 102. The connecting parts 125 may be spaced by a predetermined interval to face each other. The control valve part 123 may be operated by the second actuator 121. When the control valve part 123 is operated, the control valve part 123 may be placed in a separation space between the connecting parts 125 to block the fuel passage 102.

The control unit 130 may be connected to each of the first actuator 111, the measuring part 117, the second actuator 121, and a dashboard 140. Capacitance value of genuine fuel may be stored in the control unit 130.

A method of discriminating reformulated fuel by using an apparatus of discriminating reformulated fuel will be described in detail as follows.

Method of Discriminating Reformulated Fuel

Referring to FIGS. 1 and 3 together, when the fuel is injected into the fuel passage 102, the control unit 130 operates the first actuator 111 in operations S10 and S20.

The first actuator 111 may move the second electrode plate 115 toward the first electrode plate 113 to adjust a gap between the first and the second electrode plates 113 and 115. In other word, a separation distance between the first and the second plates 113 and 115 may be shortened. When the fuel is supplied between the first and the second electrode plates 113 and 115, the first and the second electrode plates 113 and 115 measure the capacitance of the fuel in the measuring part 117 to calculate a measured value in operation S30.

The measured value is delivered to the control unit 130 to determine whether the fuel is reformulated fuel or not, in operation S50. The capacitance value of genuine fuel is set in the control unit 130.

For instance, when the fuel is genuine, the control unit 130 does not deliver any signal to the fuel control valve unit 120 and the dashboard 140. Accordingly, the genuine fuel may pass the fuel control valve unit 120 and be stored in a fuel storage (not shown).

For another instance, when the fuel is reformulated, the control unit 130 delivers a signal to the second actuator 121 of the fuel control valve unit 120. The second actuator 121, which received the signal, may operate to allow the control valve part 123 to block the fuel passage 102, in operation S60. Furthermore, the control unit 130 delivers the signal to the dashboard 140, and a warning lamp 142 of the dashboard 140 turns on, so that users may notice whether reformulated fuel is injected or not, in operation S70.

Figure 4:
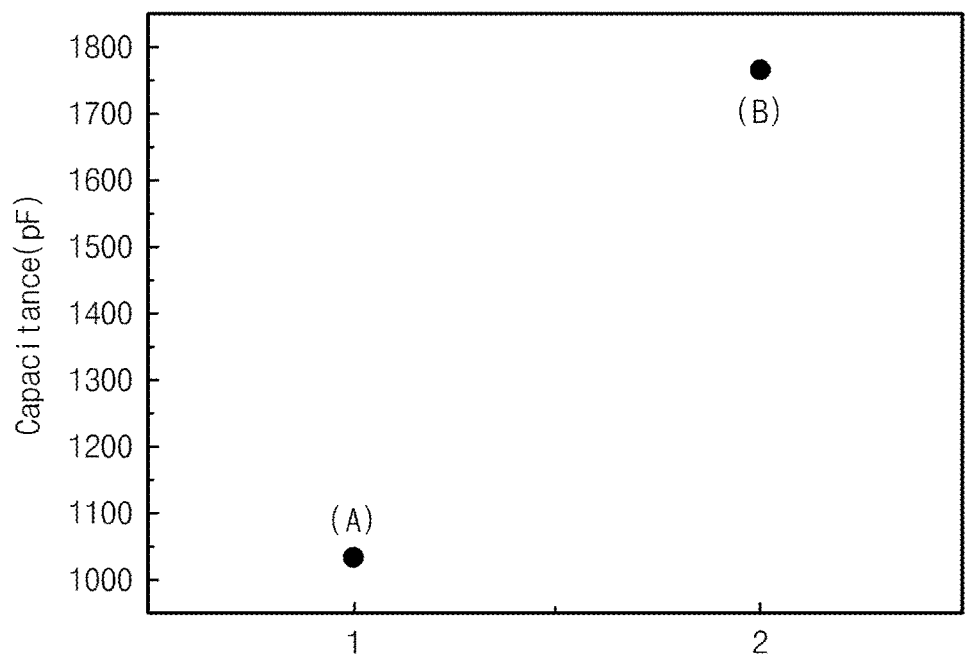
FIG. 4 is a graph showing capacitances of genuine gasoline and reformulated gasoline according to an embodiment of the present invention.

FIG. 4 is a graph showing capacitances of genuine gasoline and reformulated gasoline according to an embodiment of the present invention.

The first electrode plate (see 113 in FIG. 2) and the second electrode plate (see 115 in FIG. 2) have an area of about 80 mm×about 80 mm, and measurement was taken by applying the alternating current voltage with a frequency of 100 kHz. Referring to FIG. 4, genuine gasoline A and reformulated gasoline B are comparatively measured, and the reformulated gasoline B is cenox. The cenox consists of 90% of genuine gasoline and 10% of methanol.

As a result, the genuine gasoline A has the capacitance value of 1,030 pF, and the reformulated gasoline B has the capacitance value of 1,762.2 pF. The discrimination between the genuine gasoline A and the reformulated gasoline B is possible by using the capacitance values thereof, so that the discriminating apparatus may detect and block the inflow of the reformulated gasoline by setting the capacitance value of the genuine gasoline therein.

Figure 5:
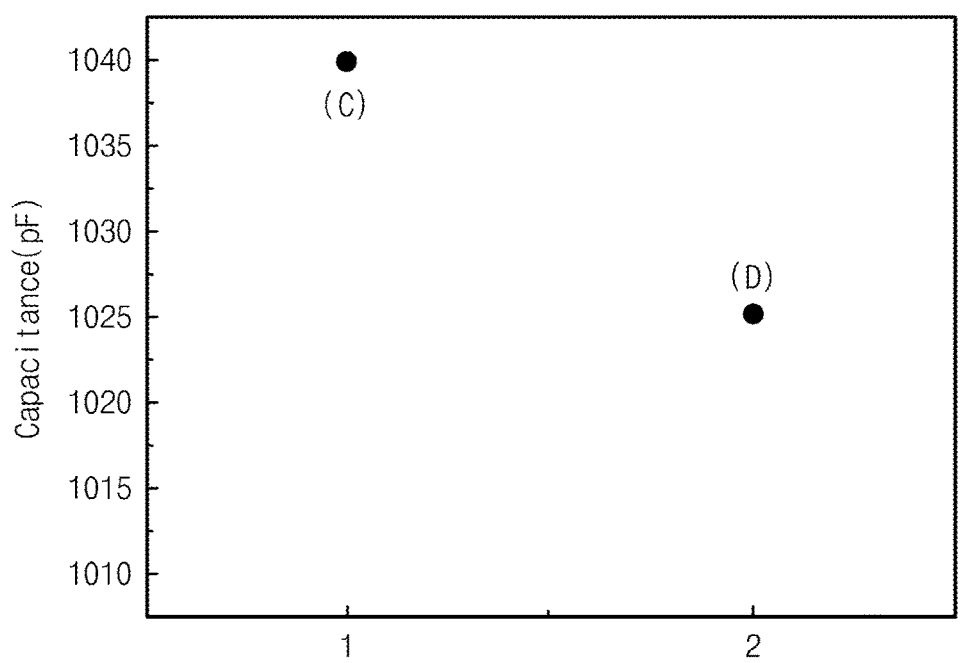
FIG. 5 is a graph showing capacitances of genuine diesel and reformulated diesel according to an embodiment of the present invention.

FIG. 5 is a graph showing capacitances of genuine diesel and reformulated diesel according to an embodiment of the present invention.

The first electrode plate (see 113 in FIG. 2) and the second electrode plate (see 115 in FIG. 2) have an area of about 80 mm×about 80 mm, and measurement was taken by applying the alternating current voltage with a frequency of 100 kHz. Referring to FIG. 5, genuine diesel C and reformulated diesel D are comparatively measured. The reformulated diesel D is generally produced by mixing genuine diesel with kerosene, and lubricant may be added thereto to compensate for the viscosity difference between the genuine diesel and the reformulated diesel. The reformulated diesel D consists of 30% of diesel, 60% of kerosene, and 10% of lubricating oil.

As a result, the genuine diesel C has the capacitance value of 1,040 pF, and the reformulated diesel D has the capacitance value of 1,025.2 pF. The discrimination between the genuine diesel C and the reformulated diesel D is possible by using the capacitance values thereof, so that the discriminating apparatus may detect and block the inflow of the reformulated diesel by setting the capacitance value of the genuine diesel therein.

Figure 6:
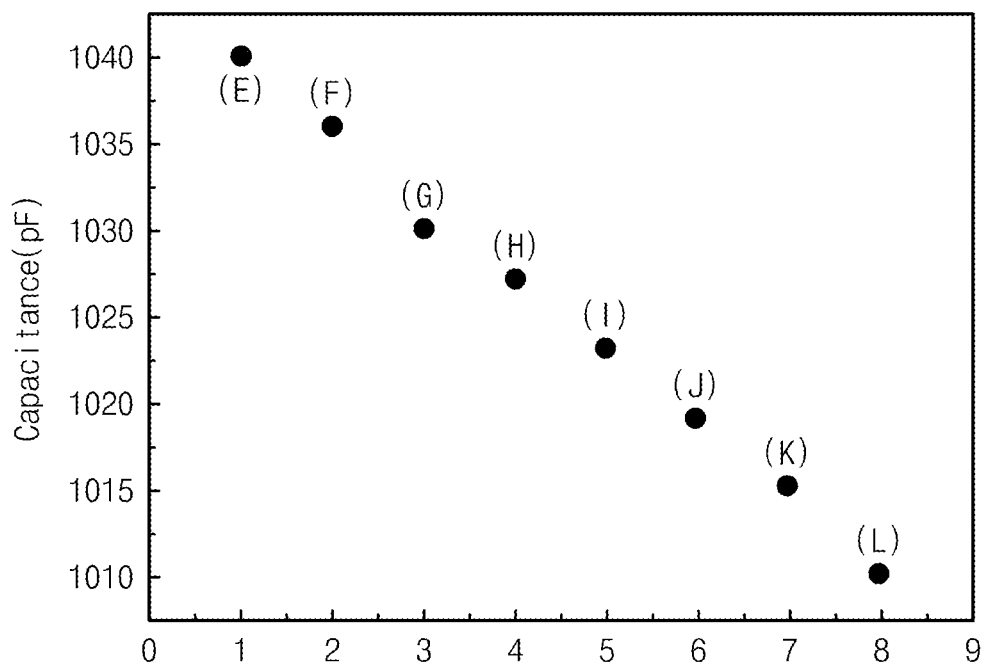
FIG. 6 is a graph showing capacitances of diesel mixed with kerosene for each concentration according to an embodiment of the present invention.

FIG. 6 is a graph showing capacitances of diesel mixed with kerosene at each mixing ratio according to an embodiment of the present invention.

TABLE 1

| EXAMPLES | DIESEL | KEROSENE | CAPACITANCE |
|---|---|---|---|
| E | 100% | 0% | 1040 pF |
| F | 95% | 5% | 1036 pF |
| G | 90% | 10% | 1030 pF |
| H | 80% | 20% | 1027 pF |
| I | 70% | 30% | 1023 pF |
| J | 60% | 40% | 1019 pF |
| K | 50% | 50% | 1015 pF |
| L | 0% | 100% | 1010 pF |

The first electrode plate (see 113 in FIG. 2) and the second electrode plate (see 115 in FIG. 2) have an area of about 80 mm×about 80 mm, and measurement was taken by applying the alternating current voltage with a frequency of 100 kHz. Referring to FIG. 6, it can be observed that the discrimination between genuine diesel E and reformulated diesel F, G, H, I, J, K, and L is possible by using the capacitance values thereof. As a result, it is possible to discriminate the genuine diesel E from the reformulated diesel F, G, H, I, J, K, and L by using the capacitance values thereof. Accordingly, the discriminating apparatus may set a capacitance value of the genuine diesel therein to detect and block the inflow of the reformulated diesel.

According to an embodiment of the present invention, an apparatus and method of discriminating reformulated fuel may automatically block the injection of the reformulated fuel by determining whether the fuel is the reformulated fuel, and allow a user to check whether the reformulated fuel is injected or not through a warning lamp of a dashboard.

The description of the present invention is intended to be illustrative, and those with ordinary skill in the technical field of the present invention will be understood that the present invention can be carried out in other specific forms without changing the technical idea or essential features. Therefore, the embodiments described above include exemplary in all respects and not restrictive, but it should be understood.

What is claimed is:

1. An apparatus of discriminating reformulated fuel, the apparatus comprising:
a fuel sensing unit comprising first and second electrode plates which are spaced and face each other, and a measuring part connected to the first and second electrode plates;
a fuel control valve unit comprising a control valve part blocking a fuel passage and a second actuator driving the control valve part; and
a control unit connected to the measuring part and the second actuator, and operating the second actuator based on a capacitance measured from the measuring part,
wherein the fuel sensing unit further comprises a first actuator allowing the second electrode plate to move toward the first electrode plate to reduce a separation distance between the first electrode plate and the second electrode plate.

2. The apparatus of claim 1, wherein the fuel sensing unit is disposed closer to a fuel inlet of the fuel passage than the fuel control valve unit.

3. The apparatus of claim 1, wherein the first electrode plate and the second electrode plate are disposed in parallel with a surface of the fuel passage.

4. The apparatus of claim 1, wherein the first and the second electrode plates are made of aluminum.

5. The apparatus of claim 1, wherein the fuel control valve unit further comprises a first connecting part and a second connecting part which face each other and respectively disposed on one side wall and the other side wall of the fuel passage,
wherein the first connecting part and the second connecting part have a space therebetween, and the control valve part is disposed in the space between the first and second connecting parts to block the fuel passage.

6. The apparatus of claim 1, further comprising a dashboard which is connected to the control unit and has a warning lamp receiving a signal from the control unit to indicate a warning when reformulated fuel is injected.

7. A reformulated fuel discrimination apparatus, the apparatus comprising:
a fuel sensor comprising first and second electrode plates which are spaced and face each other, and a measuring part connected to the first and second electrode plates;

a fuel control valve assembly comprising a control valve part blocking a fuel passage and a second actuator driving the control valve part; and a controller connected to the measuring part and the second actuator, and operating the second actuator based on a capacitance measured from the measuring part, wherein the fuel sensor further comprises a first actuator allowing the second electrode plate to move toward the first electrode plate to reduce a separation distance between the first electrode plate and the second electrode plate.

8. The apparatus of claim 7, wherein the fuel sensor is disposed closer to a fuel inlet of the fuel passage than the fuel control valve assembly.

9. The apparatus of claim 7, wherein the first electrode plate and the second electrode plate are disposed in parallel with a surface of the fuel passage.

10. The apparatus of claim 7, wherein the first and the second electrode plates are made of aluminum.

11. The apparatus of claim 7, wherein the fuel control valve assembly further comprises a first connecting part and a second connecting part which face each other and respectively disposed on one side wall and the other side wall of the fuel passage, wherein the first connecting part and the second connecting part have a space therebetween, and the control valve part is disposed in the space between the first and second connecting parts to block the fuel passage.

12. The apparatus of claim 7, further comprising a dashboard which is connected to the controller and has a warning lamp receiving a signal from the controller to indicate a warning when reformulated fuel is injected.

* * * * *